United States Patent [19]

Greenblatt

[11] Patent Number: 4,539,005
[45] Date of Patent: Sep. 3, 1985

[54] BLOOD INFUSION APPARATUS AND METHOD

[76] Inventor: Gordon M. Greenblatt, 5533 N. Third St., Phoenix, Ariz. 85012

[21] Appl. No.: 544,984

[22] Filed: Oct. 24, 1983

[51] Int. Cl.³ .............................. A61M 5/00
[52] U.S. Cl. ..................... 604/141; 128/DIG. 12; 222/95; 222/94; 248/222.2
[58] Field of Search ............... 604/141, 146, 142, 132, 604/133, 181–186, 217, 49, 80, 82; 222/92, 94, 95, 103, 105, 386.5; 128/672, DIG.20, DIG.12, DIG. 13; 248/220.2, 222.4, 225.2, 243, 248

[56] References Cited

U.S. PATENT DOCUMENTS

| | | | |
|---|---|---|---|
| 1,852,598 | 4/1932 | Vogt | 248/222.2 |
| 2,594,639 | 4/1952 | Gossett | 604/80 |
| 3,640,277 | 2/1972 | Adelberg | 128/DIG. 12 |
| 3,895,741 | 7/1975 | Nugent | 604/141 X |
| 4,039,039 | 8/1977 | Gottfried | 128/DIG. 20 |
| 4,090,514 | 5/1978 | Hinck et al. | 128/DIG. 12 |

Primary Examiner—Stephen C. Pellegrino
Attorney, Agent, or Firm—Cahill, Sutton & Thomas

[57] ABSTRACT

An apparatus for rapid infusion of blood or other fluid into a patient provides a pneumatic bladder supported within a housing having a rigid back and two rigid sides attached thereto. A hinged door with a clear, rigid window therein supports on its inner surface one or two unit bags containing fluid, such as centrifuged blood cells and/or saline solution. Closing of the door and locking of a latch presses the unit bag against the pneumatic bladder, which is rapidly inflated by means of a foot pump up to a maximum pressure determined by a relief valve that prevents overinflation of the pneumatic bladder. Opening of an evacuation valve provides nearly instant deflation of the pneumatic bladder, allowing rapid removal of the first unit bag, replacement of it by a full unit bag, and rapid reinflation of the bladder and diffusion of successive unit bags of fluid into the patient.

12 Claims, 8 Drawing Figures

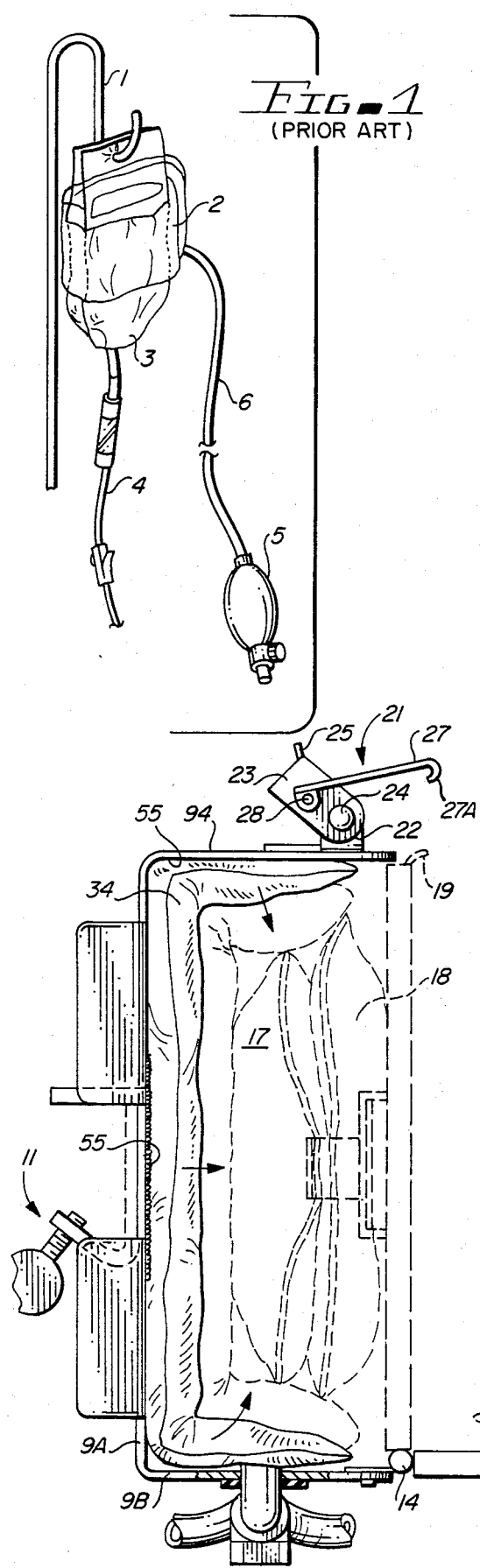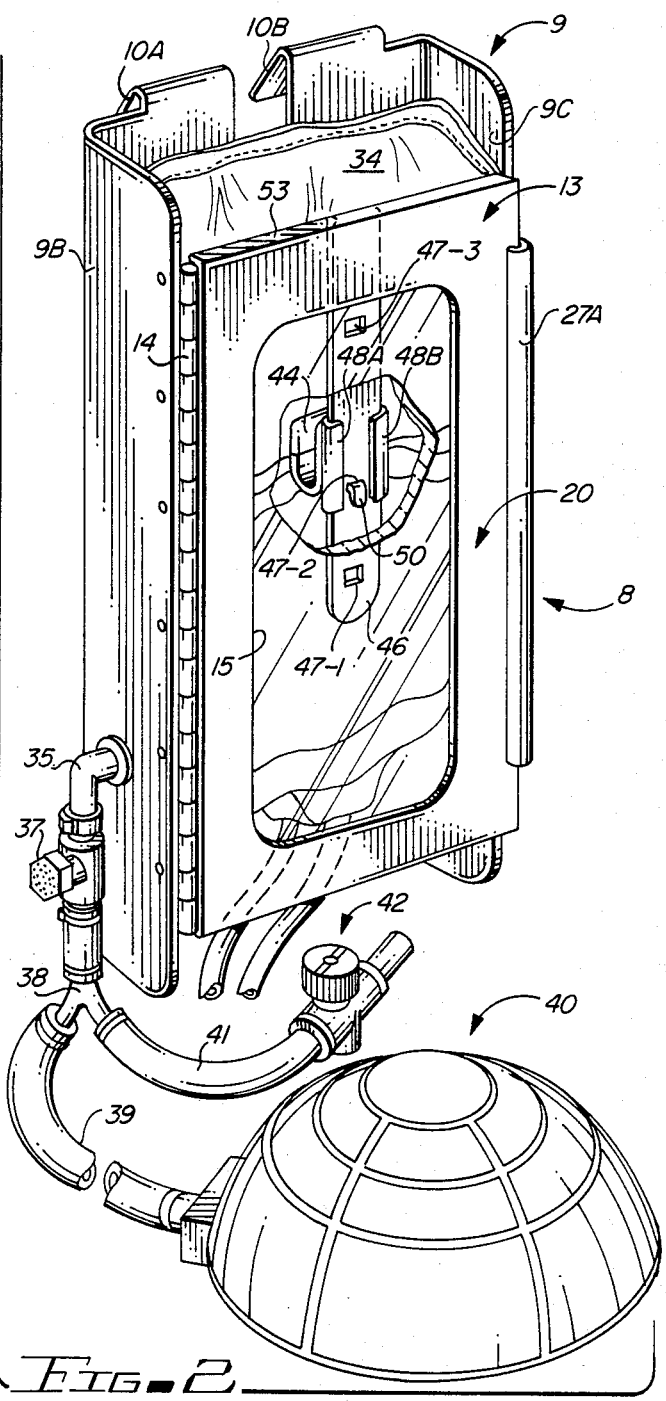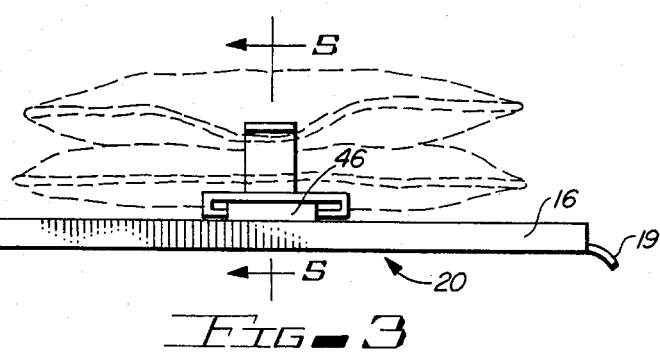

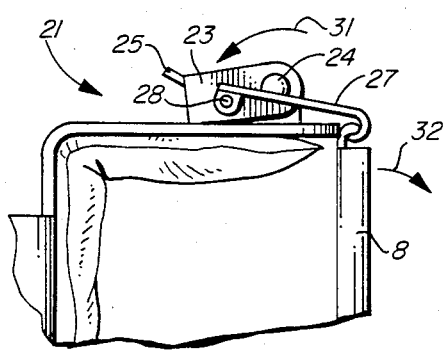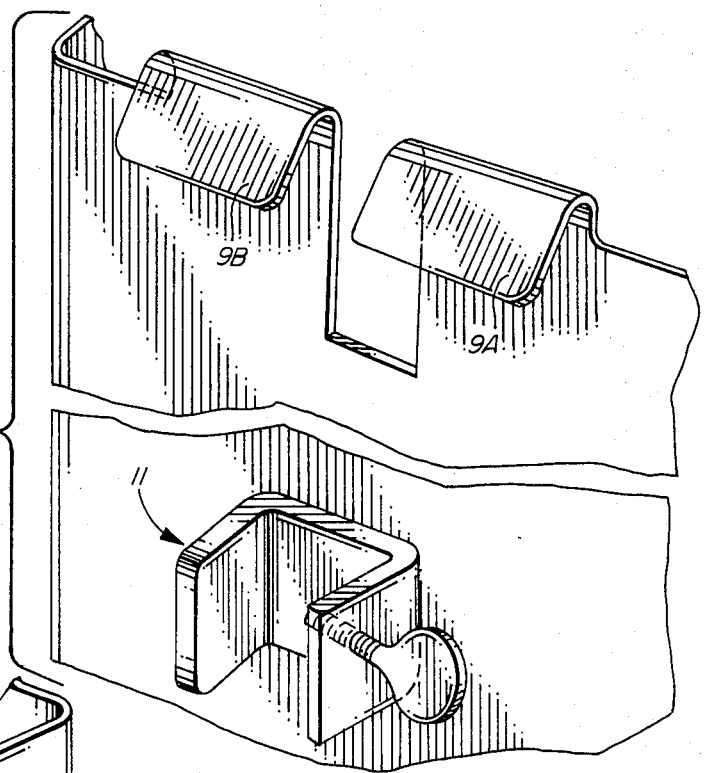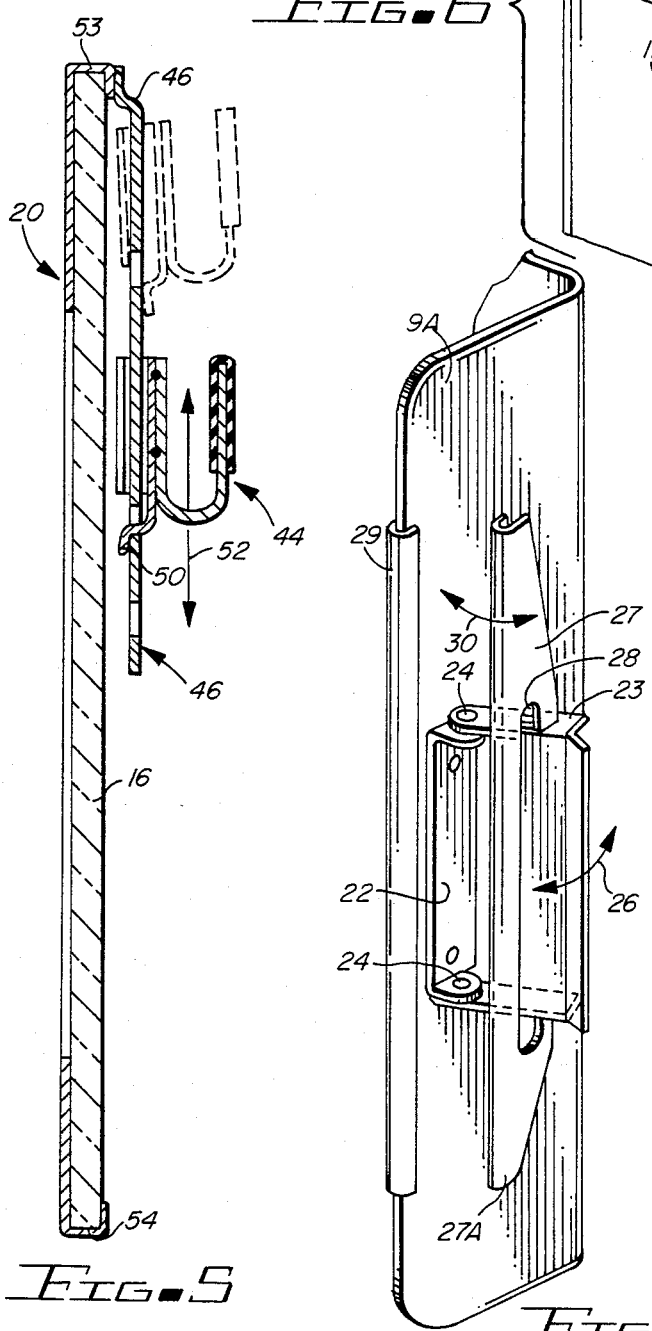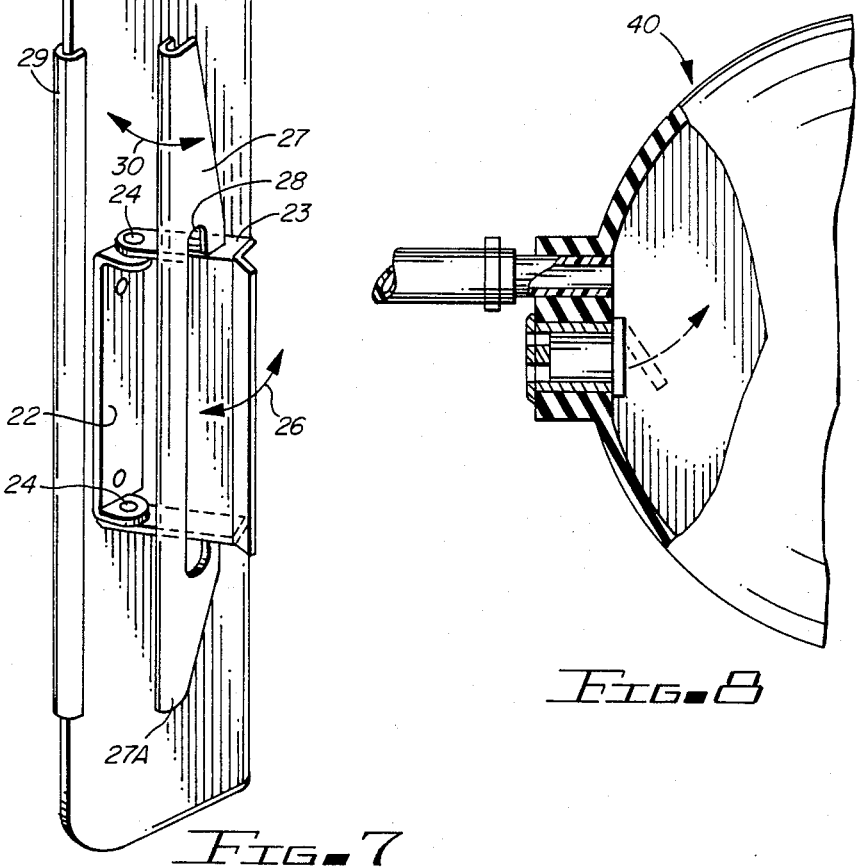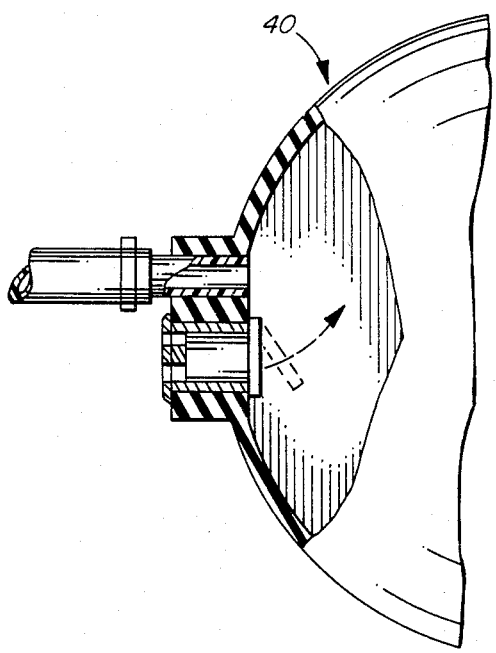

BLOOD INFUSION APPARATUS AND METHOD

BACKGROUND OF THE INVENTION

The invention relates to blood infusion apparatus for rapid infusion of life saving fluids into a patient, and more particularly to improved blood infusion boxes containing a bladder against which unit bags of life sustaining fluids are pressed by means of a front door and are inflated to facilitate more rapid infusion of the fluid than occurs action of gravity.

The most common technique for rapid infusion of blood and other life sustaining fluids in the United States, and for that matter, in the world, is use of sleeve type infusion bags of the type manufactured by Baxter Travenol. Roughly 65 million of the sleeve-type infusion bags have been sold around the world in the last dozen or so years. They are ordinarily suspended by a hook on an infusion stand. Unit bags containing the fluid to be infused are inserted into the deflated sleeve, which then is inflated by means of a small hand bulb which is repeatedly squeezed by an attendant or whoever happens to be available to squeeze it. This device has several disadvantages. The inflatable sleeve or "cuff" expands in all directions so that a large volume of air is necessary for effective pressurization. The sleeve type infusion bladder is usually suspended by a single loop or hook from the infusion stand, leading to rotation and instability of the infusion system. Furthermore, it is necessary to completely deflate the sleeve type infusion bladder in order to allow access to or removal of the unit bag containing the life sustaning fluid to be infused. Furthermore, it is usually difficult to see when the blood or fluid in the unit bag is nearing exhaustion. Usually, if red blood cells must be infused, they are initially in the form of a sticky solution, since blood received from donors is ordinarily centrifuged to separate the different useful components thereof. When red blood cells are required, the sticky red fluid must be mixed with saline solution and brought up to body temperature before it reaches the infusion needle. Often, a unit bag of blood cells are infused with a unit bag of saline solution. Typically, the unit bag of saline solution is manually squeezed into and mixed with the red blood cells in, for example, a one liter unit bag. This is a bothersome, time-consuming procedure.

Typically, due to the coldness and high viscosity of the blood cells (which have been kept cold in a refrigerator), a rather high level of pressure is required in the sleeve-type infusion bladder. Another problem with use of the sleeve type infusion bladders is that the abovementioned hand bulb type pumps usually require a person, such as a nurse, or sometimes even a physician, to spend his or her very valuable time simply operating the hand pump.

It should be appreciated that medical personnel who have to rapidly infuse life sustaining fluids frequently must use infusion equipment under extreme emergency conditions. Sometimes, two or three liters or, in some cases, even up to eight or ten liters of life sustaining fluid have to be transferred very quickly into the patient. The amount of time required to set up the infusion apparatus may be critical. In some instances, many liters of blood have to be infused into a patient within a half hour of time in order to save the patient's life. The environment in which emergency rapid blood infusion must be accomplished can include hospital emergency rooms, wherein nurses, paramedics, etc., are available to set up and operate the infusion devices. In other cases, personnel and emergency vehicles have been sent to the scene of an accident, whereat the infusion devices must be rapidly set up and operated by available personnel. In many instances, the efforts of an extremely valuable person, such as a paramedic or even a surgeon may be required to keep pumping the hand pump in order to keep the sleeve type infusion bladder adequately pressurized. This is obviously a serious problem if that person has to interrupt other medical tasks which must be performed often under the pressure of inadequate available time.

Under the pressure of situations under which blood must be rapidly infused under emergency circumstances, occasionally the squeeze bulb type pumps are not continuously operated, and sometimes they are forgotten. This can result in severe consequences to the patient if he does not receive an adequate amount of the fluid being infused in an adequate amount of time, or if the fluid being infused becomes warm and then contaminated due to bacterial action.

As a result of the difficulties that have been experienced with the above-mentioned sleeve-type infusion bladders, personnel that have to administer blood or other life-sustaining fluids to patients under emergency circumstances frequently have a very "negative" attitude about blood infusion tasks because of bad experiences that they have had resulting from the inadequacies of the blood infusion equipment used, especially the large amount of time that has been required to set up sleeve type blood infusion apparatus.

In England, a device known as the "Norfolk and Norwich Infusion Box" and described in *Anesthesia*, Volume 35, pages 1211–1214, has grealy improved the speed and reliability of infusion procedures. The device, referred to herein as an "infusion box", consists of a rigid back wall, two rigid side walls, and a hinged door at the front with a rigid transparent window therein. When in use, the door is held shut with a quick-release latch. Expansion knobs at the top of the back wall and at the top of the back surface of the door support an infusion bladder known as a Fenwall Infuser. A blood or fluid container is suspended from the knob on the back of the door. The door is closed and secured by the quick release latch, and the infusion bladder is inflated in the usual manner by means of the squeeze bulb hand pump. A major advantage of this system is that a much smaller volume of air is necessary to adequately pressurize the infusion bag. Furthermore, since the blood containing "unit bag" is not placed within the infusion sleeve, its contents are easily visible through the transparent door. Although this device is being used to some extent in Great Britain, attempts to introduce it to the market in the United States have completely failed, due to various shortcomings of the Norfolk and Norwich infusion boxes which have been introduced to date. Several different sizes of "unit bags" are commonly used for life-sustaining fluids, including half liter and liter bags; it is essential that an infusion box be able to accommodate either. The prior models of the Norfolk and Norwich Infusion Box include an awkward, adjustable, unit bag supporting device that extends well above the upper end of the infusion box. It should be appreciated that in a typical emergency environment in which blood infusion apparatus is used, whatever infusion apparatus is used must have a great deal of physical strength and durability, or else it soon will be bent, broken otherwise damaged. Medical liability laws in the United States are much more severe than those in Great Britain, and introduction of any equipment that has even minor shortcomings that may result in injury to either the patients on which the equipment is being used or the personnel operating them can subject physicians, hospitals, ambulance companies, or the state to enormous legal liability. Equipment with even minor apparent shortcomings that might cause such injury and result in such liability will not be accepted by the U.S. market.

The available models of the Norfolk and Norwich Infusion Box, although they do avoid the long "set up" time of the sleeve type infusion bladders, nevertheless do not avoid the problems of requiring a person almost to continuously operate the squeeze bulb pump. Furthermore, these models are easily damaged in the environments in which they are stored and operated. The reaction of U.S. medical supply companies, hospital personnel, physicians, has generally been that they are not interested in adopting the Norfolk and Norwich device, and instead prefer to continue using the sleeve type infusion bags, which, although they typically have a life of only approximately one month due to the rough treatment which they usually receive, are relatively inexpensive. Furthermore, this use is so common in the medical community that, despite their shortcomings, their use does not constitute a basis for a malpractice claim.

In view of the foregoing considerations, it is clear that there has long been a great need for a greatly improved, inexpensive, highly reliable, highly durable blood infusion apparatus and method which has a short set up time, does not require large amount of time by one or more persons to keep the bladders inflated to the correct pressure, and allows rapid replacement of empty unit bags of blood or other life sustaining fluid.

It is another object of the invention to provide a greatly improved infusion box that avoids the shortcomings of the Norfolk and Norwich Infusion box and which is accepted by the United States medical emergency equipment industry.

It is another object of the invention to provide a blood infusion apparatus which avoids the need for medical equipment personnel be continuously concerned about the inflation level of the bladders which pressurize the life sustaining fluid containing bags.

SUMMARY OF THE INVENTION

Briefly described, and in accordance with one embodiment thereof, the invention provides a blood infusion apparatus and method for supporting a rigid housing having a back and two sides on a support post, supporting an inflatable bladder inside the housing, supporting a flexible bag of life-sustaining fluid, such as blood, on an inner surface of a door that is hingeably attached to a front edge of the first side, closing and locking said door tightly to press the flexible bag against the bladder, and then stepping down on a foot-actuatable air pump several times to rapidly inflate the bladder. As soon as the contents of the flexible bag have been infused into the patient, a dump valve is opened to rapidly deflate the bladder. A quick release latch is then disengaged to allow opening of the front door and exchanging of the emptied flexible bag with a new one. In order to prevent overinflation of the bladder, a relief valve having a threshold of approximately six pounds per square inch is utilized. If desired, a pressure gauge is also supplied to allow continuous monitoring of the precise air pressure in the bladder. In one embodiment of the invention, two flexible bags are hung on a slidable hook that is attached to the inside of the door, and the contents of the two flexible bags, typically saline solution in one bag and viscous red blood cell material in the other, are fed through a Y connector into a single infusion tube.

In the described embodiment of the invention, the housing is composed of a unitary piece of stainless steel. VELCRO fastening material is attached to the inner surface of the back of the housing. The inflatable bladder is attached by means of the VELCRO fastening material to the back of the housing. In order to accomodate different size unit bags of blood or life sustaining fluid, a vertical slide bar is rigidly attached to the upper portion of the front door and has a plurality of spaced tabs receiving openings therein. A slide hook having a support tab thereon is positioned at the desired height for a particular sized bag by inserting the tab into a selected one of the tab receiving holes. The door is composed of a stainless steel frame having flanges which act as a guide for receiving a thick, transparent plastic window plate. The edge of the door opposite to a door length hinge attaching the door pivotally to one of the sides has an outwardly oriented lip for engaging a quick release latch mechanism. The quick release latch mechanism has a curved flange which engages the lip, so that the door opens only partially if accidentally the latch is disengaged which the bladder is still inflated.

BRIEF DESCRIPTION OF THE DRAWINGS

FIG. 1 is a partial perspective view of a prior art blood infusion apparatus.

FIG. 2 is a partial perspective view illustrating the blood infusion apparatus of the present invention.

FIG. 3 is a partial top view of the blood infusion apparatus of FIG. 2.

FIG. 4 is a partial top view illustrating the quick release latch mechanism of the device of FIG. 2.

FIG. 5 is a section view taken along section line 5—5 of FIG. 3.

FIG. 6 is a partial perspective back view of the infusion box of FIG. 2.

FIG. 7 is a partial perspective view illustrating the quick release latch mechanism of the blood infusion box of FIG. 2.

FIG. 8 is a partial cutaway section view of the footoperating pump shown in FIG. 2.

DESCRIPTION OF THE INVENTION

Referring now to FIG. 1, the above-mentioned prior art inflatable sleeve-type bladders are illustrated. Reference numeral 1 designates a infusion stand with a hook thereon. Reference numeral 2 designates a sleeve-type infusion bladder through which a flexible bloodcontaining bag 3 is inserted while bladder 2 is uninflated. Reference numeral 4 designates a connector and tubing which leads to an intravenous needle through which the infusion of liquid is made to the patient. A squeeze bulb hand pump 5 is connected by means of a tube 6 to sleeve-type inflatable bladder 2. As previously explained, nearly continuous squeezing of squeeze bulb 5 is required to maintain enough pressure in sleeve-type bladder 2 to accomplish adequately rapid infusion of blood from bag 3 into the patient.

Referring now to FIG. 2, reference numeral 8 designates the infusion box of the present invention. It includes a stainless steel unitary housing 9 having a back 9A, a left side 9B, and a right side 9C. Two wing-like flanges 10A and 10B are attached to and integral with the top edge of back 9A. Flanges 10A and 10B are aimed downward so that infusion box 8 can be hung on a T-bar (not shown). As best seen in FIGS. 3 and 6, on the rear surface of back 9A, an adjustable clamp 11 is attached thereto so that infusion box 8 can be clamped to a vertical pole (not shown) on which the above-mentioned T-bar is rigidly attached.

The front door 13 is connected by means of a long hinge 14 to the front edge of left side 9B. A generally rectangular opening 15 in the front of door 13 is provided as a window so that the user can view the interior of infusion box 8, as subsequently explained. A thick, flat plate 16 of plexiglass or other suitable plastic such as shatterproof Lexan material is slidably inserted by means of top flange 53 and a similar bottom flange 54 on door 13 that function as guides for plastic plate 16 and also serve to reinforce front door 13. It should be appreciated that a great deal of outward pressure and force is exerted on door 13 by the flexible plastic infusion bags designated by 17 and 18 in dotted lines in FIG. 3, as subsequently explained.

As best seen in FIGS. 3, 4, and 7, a quick release latch mechanism 21 includes a stationary base 22 which is rigidly welded to the outer surface of right side 9A. A lever handle 23 is pivotally connected by pin 25 to latch base 22. A flange 25 is attached on the outer end of lever handle 23 to facilitate easy gripping by the fingers of the user who wishes to move lever handle outward in one of the directions indicated by 26 in FIG. 7. A clasp arm 27 is pivotally connected to lever handle 23 by means of pin 28, which is spaced from pin 24. Clasp arm 27 has a hook end 27A for engaging lip 19 of door 8.

As best seen in FIG. 7, hook 27A of clasp arm 27 is quite elongated, extending along three-quarters of the length of the front edge of right side 9C. A rubber shield 28 is folded around on the front edge of right side 9A to cushion the engagement of the inner surface of hook end 27A to the outer edge of right side 9A.

As indicated by arrow 30 in FIG. 7, clasp arm 27 freely pivots about pins 28 to effectuate engaging or disengaging end 27A from hook 19 of door 8.

As best seen in FIG. 4, when handle lever 23 is moved all the way in the direction of arrow 31, latching mechanism 21 becomes locked more tightly when pressure from within infusion box 8 tends to force door 8 outward to the left in the direction of arrow 32, since the axis of force along clasp 27 is below the center of pin 24 as shown in FIG. 4.

Referring now to FIGS. 2 and 3, a pneumatic bladder 34 is supported against the inner surfaces of back 9A of housing 9. Preferably, VELCRO fastening material is adhesively attached to the inner surface of back 9A and matching VELCRO fastening materials attached to the outer back surface of pneumatic bladder 34 so that it remains securely supported inside of housing 9. Reference numeral 55 designate the fastened VELCRO material in FIG. 3.

The interior of pneumatic bladder 34 communicates with a pump 40 by means of a plastic tube connection and elbow 35 through a hole in left wall 9B to a relief valve 37. The opposite end of relief valve 37 is connected to a Y connector 38. One leg of Y connector 38 is connected by means of a three-eighths of an inch inside diameter flexible tube 39 to foot actuated pump 40. Pump 40 includes a one way check valve, not shown, and is available from David Clark Company of Worcester, Mass. The other leg of Y connector 38 is connected by means of a short length of tubing 41, also having an inside diameter of three-eighths of an inch to a dump valve 42.

Preferably, housing 9 is composed of 16 gauge stainless steel material. The frame of front door 13 is also composed of 0.06 inches thickness stainless steel, which is necessary to provide the durability and strength required for acceptance of a device of this type in the emergency medical industry in the United States.

Referring to FIGS. 3, 4 and 5, a vertically adjustable slide hook 44 is attached to the inner side of door 20. Slide hook 44 is supported by a rigid vertical slide bar 46, the upper end of which is rigidly attached to the upper portion of stainless steel frame of the inner side of door 20. As best seen in FIG. 2, a plurality of square tab receiving holes 47-1, 47-2 and 47-3 are disposed in vertical slide bar 46. Hook 44 has two side flanges 48A and 48B which extend around the opposed edges of vertical slide bar 46, which is offset from the inner surface of plastic plate 16. A stabilization tab 50 is rigidly attached to the bottom of slide hook 44.

The flanges 48A and 48B fit loosely around the opposed vertical edges of slide bar 46 so that slide hook 44 can be tilted enough to withdraw stabilization tab 50 out of or insert it into any of the tab receiving holes 47-1, 47-2 etc., and vertically adjust the position of slide hook 44 in the directions indicated by arrows 52 in FIG. 5. This enables slide hook 44 to be properly positioned so that 500 cubic centimeter or 1,000 cubic centimeter standard infusion bags can be quickly hung on slide hook 44 and be in the proper position with infusion box 8 when door 20 is closed and locked.

Foot pump 40, dump valve 42, relief valve 37 are available from David Clark Company of Worcester, Mass. Bladder 34 is available from David Clark Company of Worcester, Mass.

The operation and advantages of the infusion box of the present invention will now be described.

The first step in use of the infusion box 8 is to mount it on an infusion rack (not shown) referred to as an "I/V pole" so that flanges 9A and 9B (FIG. 6) are centered over the cross bar of the I/V pole and clamp 11 is tightened upon the vertical member of the I/V pole. The operator then removes all air from the infusion bag containing the life sustaining fluid to be infused, adjusts the height of slide hook 44 to accommodate the particular infusion bag, depending upon whether it is a 500 cubic centimeter bag or a 1,000 cubic centimeter bag. The operator then hangs the infusion bag on hook 44. He or she makes sure that dump valve 42 is open, closes door 20 and locks the latch assembly 21 by moving lever handle 23 in the direction of arrow 31 (FIG. 4) so that the outer end of clasp arm 27 engages lip of door 20. The operator closes dump valve 42, and steps on foot pump 40 several times to rapidly inflate bladder 34. The ⅜ inch inside diameter of Y connector 38 and the ⅜ inch inside diameter of the tubing connecting foot pump 40 to bladder 34 are adequate to allow such rapid inflation.

Ordinarily, if red blood cells are to be infused, saline solution has first been squeezed into the infusion bag containing the red blood cells. This is a very time consuming operation, which is usually done manually, although if two infusion boxes, such as 8 are available, one of them can be used to first "infuse" the saline solution into the infusion bag containing the red blood cells. Alternately, both the infusion bag containing saline solution and a separate infusion bag containing red blood cells can be hung on slide hook 44, as indicated by reference numerals 17 and 18 in FIG. 2 and door 20 can then be closed. Then, if a suitable Y connector is provided, inflation of bladder 34 will squeeze out the contents of both infusion bags into the Y connector, from which a single tube leads to the infusion needle in the patient. This technique will work if the flow of both the red blood cells and the saline solution occurs at the proper rate the Y connector.

After the contents of the infusion bag or bags have been infused into the patient, the operator can rapidly replace the empty infusion bag or bags with full ones, by opening dump valve 42, which almost instantly deflates bladder 34. The inside diamter of Y connector 38 and the ⅜ inch inside diamter of the passage through tube 41 and dump valve 42 when it is opened are adequate to allow such almost instant deflation. Then lever handle 23 can be pulled outward, releasing lip 19 of door 20 with no danger of it flying open and causing damage or injury. The empty infusion bag or bags can be quickly disconnected from the infusion tube or tubes, set aside, and a full infusion bag or bags can be installed as previously described with very little loss of time, under extreme emergency conditions.

The above-described infusion system has numerous advantages over the previously described Norfolk and Norwich infusion box. It is much more rugged in structure and safe to use and it can easily withstand the rough handling that emergency medical apparatus are frequently subjected to. Therefore, there is unlikely to be a failure or mistake that can result in injury or loss of life to a patient and result in a charge of medical malpractice. Therefore, the infusion box 8 is much more acceptable to manufacturers of medical emergency equipment in the United States. The use of foot pump 40 avoids the need to dedicate the time of valuable medical personnel to continually pumping air into the inflation bladder, and avoids the likelihood that under emergency circumstances infusion will be slowed by failure to keep the inflation bladder fully inflated. The danger of overinflation of the bladder is avoided by provision of the relief valve. The capability of keeping the bladder fully inflated without requiring an attendant to use his hands is a tremendous advantage in many emergency medical situations. The negative attitude that many medical emergency personnal have toward infusion apparatus due to the prior bad experiences with it will be avoided with the described infusion box and system. It is very easy to use, and requires very little training. With this device, the pressure in the inflation bladder can be easily maintained at a high enough level that the infusion rate is determined primarily by the diameter of the aperture in the infusion needle, not upon the pumping effort applied to the previous hand squeezed bulb pump. This makes the infusion process more predictable and reliable.

Many personnel in the medical field and the medical equipment field have, after seeing the infusion box described above in use for the first time, commented that it will make their life much easier and will save patient's lives, and have indicated to me that they consider it to be a useful and important advance in the field.

While the invention has been described with reference to a particular embodiment thereof, those skilled in the art will be able to make various modifications to the described embodiment of the invention without departing from the true spirit and scope thereof. For example, a conventional pressure gauge could be provided in addition to the relief valve to indicate to medical personnel precisely what the pressure in the inflation bladder is. In some cases, air, oxygen or nitrogen pressure lines are available in certain medical facilities, in which case this source of air pressure could be provided to inflate the bladder instead of foot pump 40.

I claim:

1. Fluid infusion apparatus comprising in combination:
   (a) a unitary rigid enclosure with a back, and first and second sides;
   (b) an inflatable bladder support in said enclosure against said back and said first and second sides for partially surrounding a flexible bag containing fluid, such as life sustaining fluid, and squeezing said flexible bag when said bladder is inflated;
   (c) a rigid, partially transparent door having hinge means for pivotally connecting one edge of said door to a front edge of said first side;
   (d) bladder supporting means for supporting sdid bladder against said back and said first and second sides;
   (e) bag supporting means for supporting said flexible bag on an inner surface of said door and for effectuating rapid attachment of said flexible bag to and removal of said flexible bag from said inner surface of said door;
   (f) latching means attached to an outer surface of said second side for quick release latching of said door to said second side;
   (g) foot operable pumping means for effectuating rapid inflation of said bladder to a pressure that effectively, rapidly squeezes fluid out of said flexible bag;
   (h) first tubing means connected to said foot operatable pumping means for conducting pressurized air from said pumping means into said bladder, said first tubing means having sufficient air conducting capacity to allow said rapid inflation;
   (i) relief valve means disposed in series relationship with said first tubing means and said pumping means for limiting the amount of air pressure in said bladder to a predetermined pressure;
   (j) dump valve means in communication with tubing and outside atmosphere for effectuating essentially immediate deflation of said bladder to the outside atmosphere, to thereby allow safe opening of said door and replacement of an empty flexible bag by a full one; and
   (k) second tubing means in open communication with said first tubing means for conducting pressurized air out of said bladder through said dump valve means, and having sufficient air conducting capacity to allow said essentially immediate deflation,
   wherein said foot operatable pumping means has sufficient pumping capacity to inflate said bladder to a predetermined infusion pressure with only several actuations of said foot operatable pumping means by the foot of an operator.

2. The fluid infusion apparatus of claim 1 including a pressure gauge connected in pressure-measuring communication with said bladder.

3. The fluid infusion apparatus of claim 1 wherein said housing and a frame of said door are comprised of stainless steel.

4. The fluid infusion apparatus of claim 3 wherein said bladder supporting means includes VELCRO fastening means connected to the inner surface of said back and said first and second sides an to an outer surface of said bladder.

5. The fluid infusion apparatus of claim 4 wherein said door has a stainless steel frame portion for slidably receiving a plate of rigid plastic window plate material and simultaneously strengthening said door, and wherein said unitary rigid enclosure is composed of stainless steel.

6. The fluid infusion apparatus of claim 5 wherein said bag supporting means includes a vertical rod attached to said frame and having a plurality of tab receiving holes, and a vertically movable, non-detachable slide hook with a support tab attached thereto for receiving and supporting one or more flexible bags at a preselected height, said support tab extending into a selected one of said tab receiving holes to support said slide hook.

7. The fluid infusion apparatus of claim 6 wherein said door includes an outwardly oriented lip along a vertical edge thereof, said latching means includes an elongated lip-engaging member for engaging said lip to prevent more than partial opening of said door in the event that said latching means is accidentally released while said bladder is pressurized and for structurally reinforcing said door when said latching means holds said door tightly closed.

8. The fluid infusion apparatus of claim 7 wherein one of said flexible bags contains thick red blood cell fluid and the other one of said flexible bags contains saline solution, an infusion needle being connected in fluid communication with both of said flexible bags by means of a Y connector.

9. The fluid infusion apparatus of claim 8 including hanging means for hanging said housing on a T-bar and clamping the back of said housing to said T-bar.

10. The fluid infusion apparatus of claim 1 wherein said relief valve limits pressure in said bladder to approximately 6 pounds per square inch.

11. A method of rapidly infusing large quantities of fluid into a patient, said method comprising the steps of:
  (a) supporting a rigid housing having a back and two sides on a support;
  (b) supporting an inflatable bladder inside said housing;
  (c) supporting a flexible bag of life-sustaining fluid on an inner surface of a door hingably attached to a front edge of said first side;
  (d) closing and locking said door to press said flexible bag against said bladder;
  (e) stepping on a foot-actuatable air pump to rapidly inflate said bladder with only several foot-strokes;
  (f) preventing overinflation of said bladder by opening a relief valve connected to said bladder if the pressure in said bladder exceeds a predetermined level; and
  (g) after infusing the life-sustaining fluid from said flexible bag into a patient, rapidly deflating said bladder by opening a dump valve and rapidly conducting air from said bladder through said dump valve, opening said door, and replacing the empty flexible bag with a full one, and repeating steps (d) through (g).

12. The method of claim 11 including supporting two flexible bags, one containing blood cell material and the other containing saline solution, on said inner surface of said door in step (c) and squeezing the blood cell material and saline solution into a Y connector and to a single infusion tube in response to pressure produced in said bladder by step (e).

* * * * *